(12) United States Patent
Ottosen et al.

(10) Patent No.: US 6,624,199 B1
(45) Date of Patent: Sep. 23, 2003

(54) AMINOBENZOPHENONES

(75) Inventors: Erik Rytter Ottosen, Ølstykke (DK); Fredrik Björkling, Helsingborg (SE)

(73) Assignee: Leo Pharmaceuticals Products Ltd. A/S, Ballerup (DK)

( * ) Notice: Subject to any disclaimer, the term of this patent is extended or adjusted under 35 U.S.C. 154(b) by 0 days.

(21) Appl. No.: 10/030,965

(22) PCT Filed: Jul. 11, 2000

(86) PCT No.: PCT/DK00/00384
§ 371 (c)(1),
(2), (4) Date: Feb. 22, 2002

(87) PCT Pub. No.: WO01/05744
PCT Pub. Date: Jan. 25, 2001

Related U.S. Application Data

(60) Provisional application No. 60/144,065, filed on Jul. 16, 1999.

(51) Int. Cl.⁷ .............................................. C07C 225/22

(52) U.S. Cl. ........................................ 514/648; 564/328

(58) Field of Search ............................ 514/648; 564/328

(56) References Cited

FOREIGN PATENT DOCUMENTS

WO  98/32730 A1  7/1998

*Primary Examiner*—Brian Davis
(74) *Attorney, Agent, or Firm*—Birch, Stewart, Kolasch & Birch LLP

(57) ABSTRACT

The present invention relates to compounds of formula I

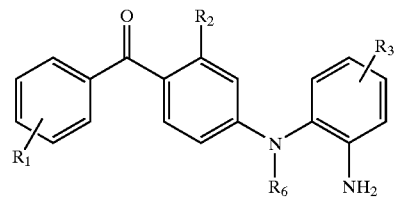

wherein $R_1$ represents one or more, similar or different substituents; $R_2$ represents hydrogen, hydroxy, halogen, alkyl, alkoxy, alkylthio, or cyano; $R_3$ represents one or more, similar or different substituents; and $R_6$ represents hydrogen or methyl; and salts thereof with pharmaceutically acceptable acids, hydrates, and solvates, and to the use of compounds of the general formula II

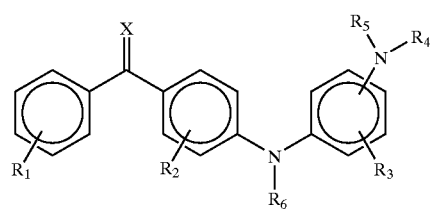

in which formula $R_1$ and $R_2$ independently represent one or more, similar or different substituents; $R_3$ represents hydrogen, halogen, hydroxy, mercapto, trifluoromethyl, amino, alkyl, alkoxy, alkylthio, alkylamino, or alkoxycarbonyl, phenyl, cyano, carboxy, or carbamoyl; $R_4$, $R_5$ and $R_6$ represent independently hydrogen, trifluoromethyl, alkyl, carbamoyl, alkoxycarbonyl, or alkaloyl; x represents oxygen, N—OH, and N—O-alkyl, dialkoxy, cyclic dialkoxy, dialkylthio, or cyclic dialkylthio, and salts thereof with pharmaceutically acceptable, non-toxic acids.

9 Claims, No Drawings

AMINOBENZOPHENONES

This application is the national phase under 35 U.S.C. § 371 of PCT International Application No. PCT/DK00/00384 which has an International filing date of Jul. 11, 2000, which designated the United States of America and was published in English. This application also claims the benefit of Provisional Application No. 60/144,065, filed Jul. 16, 1999.

FIELD OF THE INVENTION

The present invention relates to novel pharmacologically active aminobenzophenones and related compounds, a novel medical prophylaxis and treatment of acne and acne related skin diseases with aminobenzophenones, and novel compounds effective in the treatment, as well as pharmaceutical preparations containing these compounds and dosage units of such preparations.

BACKGROUND OF THE INVENTION

Previously, a series of closely related aminobenzophenones (e.g. 4-(2-amino-4-nitrophenylamino)benzophenone) have been described (Hussein, F. A. et al, Iraqi J. Sci., 22, 54–66 (1981)). However, there is no description of their uses. PCT/DK98/00008 discloses aminobenzophenone inhibitors of interleukin 1 β (IL-1 β) and tumour necrosis factor α (TNF-α) secretion in vitro, said compounds being potentially useful for treatment of inflammatory diseases in which the production of cytokines is involved in the pathogenesis, e.g. asthma, rheumatoid arthritis, psoriasis, contact dermatitis, and atopic dermatitis. Furthermore the compounds of PCT/DK98/00008 were tested in vivo for anti-inflammatory properties in the 12-O-tetradecanoylphorbol-13-acetate (TPA) induced murine chronic skin inflammation model, (De Young, L. M. et al, Agents Actions, 26, 335–341 (1989); Carlson, R. P. et al, Agents Actions, 17, 197–204 (1985); Alford, J. G. et al, Agents Action, 37, (1992); Stanley, P. L. et al, Skin Pharmacol, 4, 262–271 (1991)). In this chronic skin inflammation model the compounds had the same potency compared to the reference compound hydrocortisone.

Acne is a skin condition which is a multifactorial disease affecting the pilosebaceous follicles, characterised in increased sebum production, the formation of comedones, bacterial colonisation by especially Propionibacterium acnes, and localised inflammation. Acne vulgaris is the most common skin disorder among teenagers, but substantial numbers of adults aged 20–40 are also affected by acne. Currently available drugs for the treatment of acne include benzoyl peroxide, azelaic acid, topical and systemic antibiotics, such as fusidic acid (Fucidin®), clindamycin, erythromycin, and tetracyclin, retinoids, such as adapalene, tretinoin, isotretinoin, and hormones, such as estrogen. There are, however, serious drawbacks with these medications including teratogenicity, skin irritation, photosensibilisation, etc., cf. Table 1 below.

Because of the negative psychosocial consequences for the affected individual, and the relatively limited numbers of drugs available for topical treatment of acne and the severity of the known side effects of these drugs, the provision of new medicaments for adequate therapy of acne is very important.

The present inventors have surprisingly found that selected aminobenzophenones including novel compounds having the general formula I below are effective anti-acne agents in both in vitro and in vivo models of acne and acne related disorders with a further potential for being useful as MAP kinase inhibitors and in the treatment of diseases connected with interleukin 1 β (IL-1 β) and tumour necrosis factor α (TNF-α) secretion. These findings suggest that an inhibitor of interleukin 1 β (IL-1 β) and/or tumour necrosis factor α (TNF-α) secretion (or an inhibitor of intra/extracellular? MAP kinase) is useful in the preparation of a medicament for the treatment and/or prophylaxis of acne and related skin disorders.

SUMMARY OF THE INVENTION

The present invention is directed to novel compounds represented by the general formula I

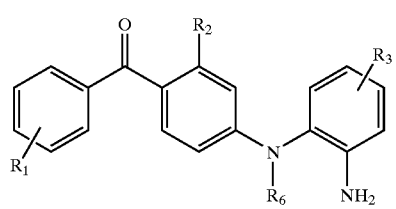

wherein $R_1$ represents one or more, similar or different substituents selected from the group consisting of hydroxy, halogen including F, Cl, Br, and I, $(C_1-C_5)$alkyl, $(C_1-C_5)$alkoxy, $(C_1-C_5)$alkylthio, and cyano; $R_2$ represents hydrogen, hydroxy, halogen including F, Cl, Br, and I, $(C_1-C_5)$alkyl, $(C_1-C_5)$alkoxy, $(C_1-C_5)$alkylthio, or cyano; $R_3$ represents one or more, similar or different substituents selected from the group consisting of halogen, including F, Cl, Br, and I, hydroxy, mercapto, trifluoromethyl, $(C_1-C_5)$alkyl, $(C_1-C_5)$alkoxy, $(C_1-C_5)$alkylthio, and cyano; and $R_6$ represents hydrogen or methyl; and salts thereof with pharmaceutically acceptable acids, hydrates, and solvates.

DETAILED DESCRIPTION OF THE INVENTION

Preferred Embodiments

In compounds of formula I it is preferred that $R_1$, $R_2$ and $R_3$ independently represent similar or different substituents selected from the group consisting of halogen including F, Cl, Br, and I, and $(C_1-C_5)$alkyl. More preferably $R_1$ represents methyl, $R_2$ and $R_3$ represent halogen, preferably F, Cl, or Br, and $R_6$ represent hydrogen.

Further preferred compounds of general formula I are compounds wherein $R_1$, $R_2$, and $R_3$ represent one substituent, $R_1$ and $R_2$ preferably being in the ortho position.

Specific compounds of formula I are:

4-(2-Amino-4-bromophenylamino)-2-chloro-2'-methylbenzophenone (Compound 101);

4-(2-Amino-4-fluorophenylamino)-2-chloro-2'-methylbenzophenone (Compound 102);

4-(2-Aminophenylamino)-2,2'-dichloro-4'-methoxybenzophenone (Compound 112);

4'-(2-Aminophenylamino)-2,2',3-trichloro-4-methoxybenzophenone (Compound 113);

4'-(2-Aminophenylamino)-2,2',6-trichloro-4-methoxybenzophenone (Compound 114);

4-(2-Aminophenylamino)-2-chloro-2'-hydroxybenzophenone (Compound 115);

4-(2-Aminophenylamino)-2-chloro-2'-fluorobenzophenone (Compound 116);

4-(2-Aminophenylamino)-2,2'-dichloro-4'-hydroxybenzophenone (Compound 117);

4-(2-Amino-4-bromophenylamino)-2-chloro-4'-ethoxy-2'-methylbenzophenone (Compound 118);

4-(2-Amino-4-bromophenylamino)-2-ethoxy-2'-methylbenzophenone (Compound 119);

4'-(2-Aminophenylamino)-2,2',4-trichloro-6-hydroxybenzophenone (Compound 120);

4-(2-Amino-5-hydroxyphenylamino)-2-chloro-2'-methylbenzophenone (Compound 121);

4-(2-Aminophenylamino)-2-fluoro-2'-methoxybenzophenone (Compound 122);

4-(2-Aminophenylamino)-2-fluoro-2'-methylbenzophenone (Compound 123);

4-(2-Amino-5-methoxyphenylamino)-2-chloro-2'-methylbenzophenone (Compound 124);

4-(2-Amino-5-chlorophenylamino)-2-chloro-2'-methylbenzophenone (Compound 125);

4-(2-Amino-4-(trifluoromethyl)phenylamino)-2-chloro-2'-methylbenzophenone (Compound 126);

4-(2-Amino-3-fluorophenylamino)-2-chloro-2'-methylbenzophenone (Compound 127);

4-(2-Amino-N-methyl-phenylamino)-2-chloro-2'-methylbenzophenone (Compound 128);

4-(2-Aminophenylamino)-2,2'-dimethylbenzophenone (Compound 129);

4-(2-Amino-4-fluoro-N-methyl-phenylamino)-2-chloro-2'-methylbenzophenone (Compound 130);

4-(2-Amino-6-methylphenylamino)-2-chloro-2'-methylbenzophenone (Compound 131);

4-(2-Amino-4-methoxyphenylamino)-2-chloro-2'-methylbenzophenone (Compound 132);

4-(2-Aminohenylamino)-2-chloro-3'-fluoro-2'-methylbenzophenone (Compound 133);

4-(2-Amino-4-bromophenylamino)-2-chloro-2',3'-dimethylbenzophenone (Compound 134);

4-(2-Amino-4-bromophenylamino)-4'-n-butyl-2-chloro-2'-methylbenzophenone (Compound 135);

4-(2-Amino-4-bromophenylamino)-2,4'-dichloro-2'-methylbenzophenone (Compound 136);

4-(2-Amino-4-bromophenylamino)-2-fluoro-2'-methylbenzophenone (Compound 137);

4'-(2-Amino-4-bromophenylamino)-2'-chloro-2,4,5-trimethylbenzophenone (Compound 138);

4-(2-Amino-4-bromophenylamino)-2-chloro-4'-fluoro-2'-methylbenzophenone (Compound 139);

4-(2-Amino-4-bromophenylamino)-2-chloro-2',5'-dimethylbenzophenone (Compound 140);

4-(2-Amino-4-bromophenylamino)-2,3'-dichloro-2'-methylbenzophenone (Compound 4-(2-Amino-4-bromophenylamino)-2-fluoro-4'-methoxy-2'-methylbenzophenone Compound 142), and their salts with pharmaceutically acceptable acids, hydrates, and solvates.

The compounds of formula I are useful in the treatment and/or prophylaxis of acne and acne related skin disorders.

Furthermore, the present invention is directed to the use of compounds disclosed in PCT/DK98/00008 and represented by the general formula II

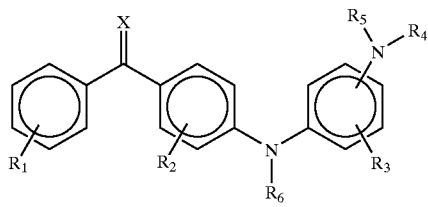

in which formula $R_1$ and $R_2$ independently represent one or more, similar or different substituents selected from the group consisting of hydrogen, halogen, hydroxy, mercapto, trifluoromethyl, amino, $(C_1-C_5)$alkyl, $(C_1-C_5)$alkoxy, $(C_1-C_5)$alkylthio, $(C_1-C_5)$alkylamino and $(C_1-C_5)$alkoxycarbonyl, cyano, carbamoyl, phenyl, or nitro; and $R_2$ can further represent carboxy; $R_3$ represents hydrogen, halogen, hydroxy, mercapto, trifluoromethyl, amino, $(C_1-C_5)$alkyl, $(C_1-C_5)$alkoxy, $(C_1-C_5)$alkylthio, $(C_1-C_5)$alkylamino, or $(C_1-C_5)$alkoxycarbonyl, the C-content of which can be from 1 to 5, phenyl, cyano, carboxy, or carbamoyl; $R_4$, $R_5$ and $R_6$ represent independently hydrogen, trifluoromethyl, $(C_1-C_5)$alkyl, carbamoyl, $(C_1-C_5)$alkoxycarbonyl, or alkaloyl, the C-content of which can be from 1 to 5; X represents oxygen, N—OH, and N—O-alkyl, dialkoxy, cyclic dialkoxy, dialkylthio, or cyclic dialkylthio, in which groups the C-content can be from 1 to 5, preferably X represents oxygen, N—OH, or N—O-alkyl wherein the C-content can be from 1 to 5; and salts thereof with pharmaceutically acceptable, non-toxic acids; for the preparation of a medicament for the prophylaxis and/or treatment of acne and acne related skin disorders.

It is preferred to use compounds of general formula II wherein $R_1$ and $R_2$, represent one substituent, said substituent preferably being in the ortho position. It is furthermore preferred that the group —$NR_4R_5$ is in the ortho position.

The compounds of formula I and II herein can be used in the form of their salts which are formed with pharmaceutically acceptable inorganic or organic acids, such as hydrochloric, hydrobromic and hydroiodic acid, phosphoric acid, sulphuric acid, nitric acid, p-toluene-sulphonic acid, methanesulphonic acid, formic acid, acetic acid, propionic acid, citric acid, tartaric acid, succinic acid, benzoic acid, maleic acid, these examples being considered as non-limiting for the invention.

Specific compounds of formula II useful as medicaments for the treatment and/or prophylaxis of acne and acne related skin disorders are:

4-(2-aminophenylamino)-2-chloro-2'-methylbenzophenone (Compound 103);

4-(2-aminophenylamino)-2-methoxy-2'-methylbenzophenone (Compound 104);

4-(2-aminophenylamino)-2-chloro-2'-(trifluoromethyl) benzophenone (Compound 105);

ethyl N-(2-(4-(2-methylbenzoyl)-3-chlorophenylamino) phenyl)carbamate (Compound 106);

4'-(2-aminophenylamino)-2'-chloro-4-methoxy-2,6-dimethylbenzophenone (Compound 107);

2,2,2-trifluoro-N-(2-(4-(2-methylbenzoyi)-3-chlorophenylamino)phenyl)acetamide (Compound 108);

4-(2-aminophenylamino)-2-chloro-2',6'-dimethylbenzophenone (Compound 109);

4-(2-aminophenylamino)-2-chloro-4'-fluoro-2'-methylbenzophenone (Compound 110);

4-(2-aminophenylamino)benzophenone (Compound 111);

and their salts, including salts with pharmaceutically acceptable acids as specified herein, hydrates and solvates.

As used in the specification, unless specified to the contrary, the following terms have the meaning indicated:

"Alkyl" refers to any univalent group derived from an alkane by removal of a hydrogen atom from any carbon atom, and includes the subclasses of normal alkyl (n-alkyl), i.e. primary, secondary and tertiary alkyl groups respectively, and having the number of carbon atoms specified, including for example ($C_1$–$C_5$)alkyl, ($C_1$–$C_3$) alkyl, ($C_1$–$C_2$)alkyl, methyl, ethyl, n-propyl, isopropyl, n-butyl, isobutyl, sec-butyl, and t-butyl. Alkane refers to an acyclic branched or unbranched hydrocarbon having the general formula $C_nH_{2n+2}$, and therefore consisting entirely of hydrogen atoms and saturated carbon atoms.

"Olefinic group" refers to a straight or branched acyclic hydrocarbon having one or more carbon-carbon double bonds of either E or Z stereochemistry where applicable, and having the number of carbon atoms specified. The term includes, for example, ($C_2$–$C_{15}$)olefinic group, preferably a ($C_2$–$C_{15}$)alkenyl; ($C_2$–$C_3$)olefinic group, preferably a ($C_2$–$C_3$)alkenyl; vinyl; allyl; 1-butenyl; 2-butenyl; and 2-methyl-2-propenyl. Olefinic groups having only one carbon-carbon double bond, herein called alkenyl, are preferred.

"Alkoxy" refers broadly to a radical of the formula —OR, where R is alkyl as defined above, for example ($C_1$–$C_5$) alkoxy, ($C_1$–$C_3$)alkoxy, methoxy, n-propoxy, and the like.

"Alkaloyl" refers broadly to a radical of the formula —COR where R is alkyl as defined above, for example —$COCH_3$, and —$COCH_2CH_3$.

"Alkylthio" refers broadly to a radical of the formula —SR, where R is alkyl as defined above and includes ($C_1$–$C_3$)alkylthio, methylthio, ethylthio, n-propylthio, and 2-propylthio.

"Halogen" means the same or different of fluoro, chloro, bromo, and iodo; fluoro, chloro, and bromo being preferred.

"($C_3$–$C_6$)cycloalkyl" means cycloalkyl groups having from 3–6 carbon atoms, and includes, for example, ($C_3$–$C_5$) cycloalkyl, cyclopropyl, cyclopentyl, and cyclohexyl.

"Carbamoyl" refers broadly to a radical of the formula —$CONH_2$, —CONHR, and —CONRR' where R and R' represent alkyl as defined above.

"Carboxy" refers broadly to a radical of the formula —COOH.

The phrase "the C-content of which can be from 1 to 5" is used herein to specify the number of carbon atoms in a substituent group, such as an alkyl group.

When $R_1$, $R_2$ and $R_3$ in formulae I, and II represent a phenyl group this is optionally substituted, e.g. with hydroxy; amino; nitro; cyano; halogen, preferably fluoro, chloro, or bromo; methyl; or methoxy.

Features of Acne Medication

Table 1 below summarises the various therapeutic effects and side effects of the existing drugs for treatment of acne.

TABLE 1

Features of acne medication.

| Agent | Anti-inflam. | Antibacterial | Comedolytic | Potential irritant | Teratogenic |
|---|---|---|---|---|---|
| Benzoyl peroxide* | Maybe | Yes | Somewhat | Yes | Unknown |
| Azelaic acid* | Maybe | Yes | Yes | Yes | No |
| Clindamycin* | Maybe | Yes | No | No | Probably not |
| Erythromycin* | Maybe | Yes | No | No | Unknown |
| Fusidic acid (Fucidin ®)* | Maybe | Yes | No | Yes | No |
| Tretinoin* | No | No | Yes | Yes | Maybe |
| Tetracyclin** | Yes | Yes | No | No | Yes |
| Doxycyclin** | Yes | Yes | No | No | Yes |
| Minocyclin** | Yes | Yes | No | No | Yes |
| Erythromycin** | Yes | Yes | No | No | Unknown |
| Isotretinoin** | Yes | Yes | Yes | Yes | Yes |

*Topical administration
**systemic administration

References to Table 1: Scientific American Medicine, Dec. 96, Chapter 2 Dermatology, Acne Vulgaris and Acneiform Eruptions (E. A. Abel and E. M. Faber). Lægemiddelkataloget 1996, Acnemidler pp. 197–198, (Dansk Lægemiddelinformation A/S, Copenhagen). Models in Dermatology, vol. 2, pp. 145–158, (Maibach, Lowe), Repair and Antibacterial Effects of Topical Antiseptic Agents. Models in Dermatology, vol 2, pp 59–63, (Maibach, Lowe), Anti-Acne Activity of Retinoids in the Rhino Mouse. Models in Dermatology, vol 2, pp. 35–42, (Maibach, Lowe), Evaluation of Topical Nonsteroidal Anti-inflammatory Agents. International Pharmacy Journal, Volume 9, No. 1, 1995, New Medicines, Acne vulgaris. Drugs 39 (5) 681–692, 1990, Current Views on the Aetiology, Pathogenesis and Treatment of Acne Vulgaris (L. Lever and R. Marks). Drugs 48 (1), 59–70, 1994, Acne, A Review of Optimum Treatment (N. L. Sykes and G. F. Webster).

Pharmacological Methods

To study the effect of the compound of the present invention in vivo, the following procedures were used:

For in vivo assays, the test compounds were dissolved in acetone. Adapalene was tested as a gel formulation (Differin gel 0.1%, 20–30 mg/treatment). The screening doses were 0.5 mg/ear in model 1 and 2. Exception was all-trans retinoic acid (0.01 mg/ear).

Model 1. Oxazolone-induced Contact Dermatitis in the Mouse Ear

AIM Compounds with anti-inflammatory effects in this model may be useful in treating contact eczema in man.

METHODS Groups of 5–6 mice sensitised to oxazolone 4 days before challenge with oxazolone to the right ear. The resulting oedema (right ear thickness minus left ear thickness) is measured 24, 48 and 72 hours post-challenge (PC), and neutrophil (PMN) influx is determined by the myeloperoxidase (MPO) method 72 hours post-challenge in ear biopsies. The screening dose is 0.5 mg/ear or less applied to the right ear 30 min post-challenge (+30 min). Other dosing regimes are stated.

RESULTS Results are recorded as % change from control animals using the formula: 100(T/C-1) where T=mean Oedema/MPO treated group and C=mean Oedema/MPO control group. Negative figures represent inhibition and positive stimulation. The level of significance is set at $p<0.05$ using the Mann-Whitney's U-test. Significant stimulation is stated.

| SCORE = 0 | % inhibition Oedema 48 h PC | < 25 | |
|---|---|---|---|
| = 1 | % inhibition Oedema 48 h PC | ≥ 25 | $p < 0.05$ |
| = 2 | % inhibition Oedema 48 h PC | ≥ 35 | $p < 0.05$ |
| = 3 | % inhibition Oedema 48 h PC | ≥ 45 | $p < 0.05$ |

Model 2. Tpa-induced Chronic Skin Inflammation in the Mouse Ear

AIM Compounds with anti-inflammatory effects in this model may be useful in treating chronic skin disorders in man.

METHODS In groups of 5–6 mice, ear inflammation is induced by multiple topical applications of TPA on alternate days during a 10-day period. The resulting inflammation is treated topically with compounds in acetone solution twice daily on day 8, 9 and 10 and once on day 11. Ear thickness (ET) is determined 5–6 hours after the last drug administration, the mice are sacrificed and myeloperoxidase (MPO) activity (=PMN-infiltration) is determined in ear biopsies, cf. De Young, L. M. et al, Agents Actions, 26, 335–341 (1989); Carlson, R. P. et al, Agents Actions, 17, 197–204 (1985); Alford, J. G. et al, Agents Action, 37, (1992); Stanley, P. L. et at, Skin Pharmacol, 4, 262–271 (1991).

RESULTS Results are recorded as % change from control group using the formula: 100(T/C-1) where T=mean ET/MPO treated group and C=mean ET/MPO control group. Negative figures represent inhibition and positive stimulation. The level of significance is set at $p<0.05$ using the Mann-Whitney's U-test. Significant stimulation is stated.

| SCORE = 0 | % inhibition ET | <25 | |
|---|---|---|---|
| = 1 | % inhibition ET | ≥25 | $p < 0.05$ |
| = 2 | % inhibition ET | ≥40 | $p < 0.05$ |
| = 3 | % inhibition ET | ≥50 | $p < 0.05$ |

TABLE 2

In vivo activities

| | SCORE | |
|---|---|---|
| Compound | OXA Oedema 48 hours p.c. | TPA Ear swelling |
| Erythromycin | 0 | 1 |
| Azelaic acid | 0 | 0 |
| Benzoyl peroxide | 0 | 0 |
| All-trans ret. acid | 0 | 0 |
| Compound 103 | 2 | 2 |
| Compound 106 | 2 | 2 |
| Compound 101 | 2 | 3 |

Positive numbers are inhibition, negative are stimulation

Rhino Mouse Model

The rhino mouse is an in vivo model for the study of hyperplastic and comedolytic potency of various drugs used in the treatment of acne. The rhino mouse has follicles on the skin. The orifices are distended with horny material and these structures resembles human microcomedones and are referred to as utriculi or pseudocomedones.

In the present study the effect of a number of compounds were evaluated in the rhino mouse model. All-trans retinoic acid is normally used as a positive control in the rhino mouse as this drug has been demonstrated to have a marked activity, i.e. comedolysis and epidermal thickening and this drug was included in three different concentrations in the present study. Additionally a number of marketed products used today for treatment of acne were selected and included for comparison.

The animals were treated once daily for three weeks including weekends. Animals were clinically observed daily and animal weights were recorded before start of treatment and weekly during the treatment period. Histological evaluation of the skin was performed at the end of the treatment period. Results are shown in Table 3 below.

The compounds 103 and 106 4-(2-aminophenylamino)-2-chloro-2'-methylbenzophenone and ethyl N-(2-(4-(2-methylbenzoyl)-3-chlorophenylamino)phenyl)carbamate, and the novel compounds 101 and 102 4-(2-amino-4-bromophenylamino)-2-chloro-2'-methylbenzophenone and 4-(2-amino-4-fluorophenylamino)-2-chloro-2'-methylbenzophenone), tested in 1.5% concentration in acetone all showed a comedolytic effect with reduction in number of utriculi and epidermal hyperplasia with increase in epidermal thickness and follicular epithelia. The comedolytic activity was most pronounced after treatment with compound 101 4-(2-Amino-4-bromophenylamino)-2-chloro-2'-methylbenzophenone reducing the number of utriculi with 67.4%. The effect observed for the three compounds was comparable with the effect observed after treatment with the commercial acne product Basiron® gel (benzoyl peroxide) in concentrations of 5% and 10%. However, the comedolytic activity of the tested reference compound was accompanied by skin irritancy and in contrast to this the three compounds did not induce any clinical visible skin irritancy during the three weeks treatment period. The model has been described in details, cf. Mann SJ. Hair loss and cyst formation in hairless and rhino mutant mice. Anat Rec 1971; 170: 485–90.

In conclusion the present study has shown that the compounds 4-(2-aminophenylamino)-2-chloro-2'-methylbenzophenone and ethyl N-(2-(4-(2-methylbenzoyl)-3-chlorophenylamino)phenyl)carbamate and compound 101 of the invention possess comedolytic activity without concomitant skin irritancy in contrast to the topical comedolytic agents presently being marketed. Compound 101 shows the most pronounced comedolytic activity.

Table 3. Survey giving the average % reduction in number of utriculi, average % increase in epidermal thickness during the study period for the tested drug formulations versus their respective vehicle controls or in case of commercial formulations versus untreated controls (n=6 per group)—Reference compounds.

| Drug substance | Formulation and concentration | Skin irritation YES/NO | % reduction in number of utriculi | % increase in epidermal thickness |
| --- | --- | --- | --- | --- |
| All-trans retinoic acid | 20 μg/ml in ethanol, period 1 | YES | 81.5 | 110 |
| Adapalene | Differin ™ gel 0.1% | YES | 92.7 | 202 |
| Benzoyl peroxide | Basiron ® gel 10% | YES | 62.1 | 190 |
| Benzoyl peroxide | Basiron ® gel 5% | YES | 46.1 | 178 |
| Azelaic acid | Skinoren ® cream 20% | NO | 5.7 | 75 |
| Compound 103 | 1.5% in acetone | NO | 52.5 | 120 |
| Compound 106 | 1.5% in acetone | NO | 38.3 | 146 |
| Compound 101 | 1.5% in acetone | NO | 67.4 | 203 |

These results shows that the compounds of the present invention are of similar potency compared to known reference compounds, e.g. all-trans retinoic acid with its known side effects. However, in contrast to these the compounds of the present invention show minimal skin irritation and are relatively non-toxic. Furthermore, some members of the present class of compounds show a very low absorption, thus making them especially useful in the treatment of various dermatological diseases. In general, they may be administered by oral, intravenous, intraperitoneal, intranasal, topically or transdermal routes.

Method of Preparation

The present-invention also relates to methods for preparing the desired compounds of the general formulae I and II. The compounds of the formula I may conveniently be prepared by standard procedures detailed in the art, cf. Scheme 1 in PCT/DK98/00008, and as described below, together with methods known in the art of synthetic organic chemistry, or variations thereof as appreciated by those skilled in the art.

The novel compounds of formula I, and II may be prepared using the reactions and techniques described in this section. The reactions are performed in solvents appropriate to the reagents and materials employed and are suitable for the transformations being effected. Also, in the synthetic methods described below, it is to be understood that all proposed reaction conditions, including choice of solvent, reaction atmosphere, reaction temperature, duration of experiment and work-up procedures, are chosen to be conditions of standard for that reaction, which should be readily recognised by one skilled in the art. It is understood by one skilled in the art of organic synthesis that the functionality present on various portions of the educt molecule must be compatible with the reagents and reactions proposed. Not all compounds of formula I falling into a given class may be compatible with some of the reaction conditions required in some of the methods described. Such restrictions to the substituents which are compatible with the reaction conditions will be redily apparent to one skilled in the art and alternate methods can be used.

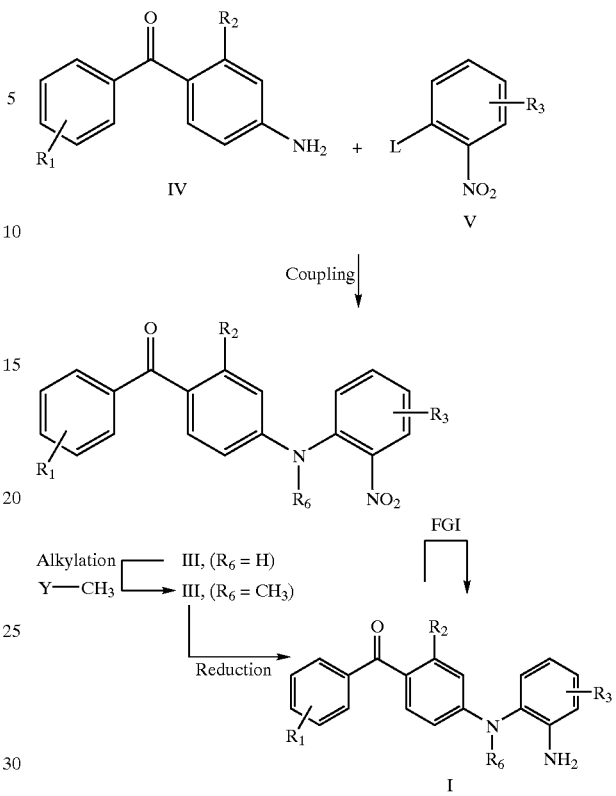

L: Br, I OSO$_2$CF$_3$, or F and Cl
Y: Cl, Br, I, OSO$_2$CF$_3$, OSO$_2$CH$_3$, or OTs
FGI: Functional group interconversion
and R$_1$, R$_2$, and R$_6$ have the above meanings.

Scheme 1

Compounds according to the present invention are preferably prepared by a process comprising coupling of an amine of the formula IV with an fluoride, chloride, bromide, iodide, or triflate with the formula V, as shown in Scheme 1, where R$_1$, R$_2$, R$_3$, and, R$_6$ are as defined in general formula I, to give a coupled product with the general formula III, except that any substituents or functional group which are potentially reactive in the coupling reaction may themselves be protected before the coupling reaction is performed and subsequently removed. This compound III may then be reduced to the corresponding amine with the general formula I by treatment with standard reducing agents. Examples of such reducing agents include, but are not limited to, stannous chloride dihydrate; hydrogen, ammonium formiate, or hydrazine hydrate and a catalytic amount of palladium on carbon.

The coupling reaction is carried out using any of the methods for the formation of diphenylamines known to one skilled in the art of organic synthesis. The preferred method is the nucleophilc aromatic substiution method which comprising coupling of an amine with an arylfluoride or arylchloride in the presence of a base, in an suitable solvent. Especially potassium-tert-butoxide (KOt-Bu), sodium-tert-butoxide (NaOt-Bu), sodium hydrid (NaH), and potassium hydride (KH) have proven to be the best bases in this process, but other bases may be used as well.

The reaction is typically performed at ambient temperature (20–25° C.) in dipolar aprotic solvents like dimethylsulfoxide (DMSO), dimethylformamide (DMF), or N-methylpyrrolidone (NMP) under an inert atmosphere like argon or nitrogen.

Alternatively, the coupling reaction can be done by the palladium catalysed amination method which comprising coupling of an amine with an arylhalogenide (iodide, bromide, triflate, or in some cases chloride) in the presence of a base, a suitable Pd source, and a suitable phosphine ligand in an inert solvent.

The palladium compound used in the process is not particularly limited, and as specific examples are palladium (II) acetate, palladium(II) chloride, palladium(II) bromide, dichlorobis(triphenylphosphine)palladium(II), tetrakis (triphenylphosphine)palladium(0), tris (dibenzylideneacetone)dipalladium(0). The preferred ligand include, but are not limited to, racemic or non-racemic 2,2'-bis(diphenylphosphino)-1,1'-binaphthyl (hereinafter referred to as BINAP), tri-o-tolylphosphine, tri-tert-butylphosphine, 1,1'-bis(diphenylphosphino)-ferrocene, bis [(2-diphenylphosphino)phenyl]ether (DPEphos), 2-dicyclohexylphosphanyl-2'-dimethylaminobiphenyl, 2-(di-tert-butylphosphino)biphenyl, and 9,9-dimethyl-4,6-bis(diphenylphosphino)xanthene (Xantphos). The amount of palladium and ligand used in this process is typically in the range 0.1 to 10% by mole relative to the amount of the aromatic halide (or triflate) used. Especially sodium-tert-butoxide (NaOt-Bu) and caesium carbonate ($Cs_2CO_3$) have proven to be the best bases in this process, but other bases may be used as well. The reaction is typically performed at elevated temperature (80–120° C.) in inert solvents like 1,4-dioxane, toluene, benzene and tetrahydrofurane under an inert atmosphere like argon or nitrogen.

Compounds according to the present invention in which $R_6$ is not hydrogen may be prepared by a process comprising coupling of an amine of the formula III ($R_6$=H) with an alkylating agent, as shown in scheme 1, where $R_1$, $R_2$, $R_3$, and, $R_6$ are as defined in general formula I, except that any substituents or functional group which are potentially reactive in the coupling reaction may themselves be protected before the coupling reaction is performed and subsequently removed.

Typically alkylating agents of the general formula $CH_3$-Y include, but are not limited to, iodides (Y=I), bromides (Y=Br), chlorides (Y=Cl) and sulfonates (Y=$OSO_2R'$, where R' represents methyl, trifluoromethyl or 4-methylphenyl).

Compounds according to the present invention may in special cases be prepared by a as simple functional group interconversion (FGI), meaning a standard process, known to those skilled in the art of organic synthesis, where a functional group in compounds with the general formula I is transformed into a different functional group in one or more synthetic steps, leading to a new compound with the general formula I. Examples of such processes are, but are not limited to, hydrolysis of an ester to give an acid under basic conditions; deprotection of an methylether to give an phenol by treatment with e.g. borontribromide ($BBr_3$); and catalytic hydrogenation of an olefin to give an saturated hydrocarbon.

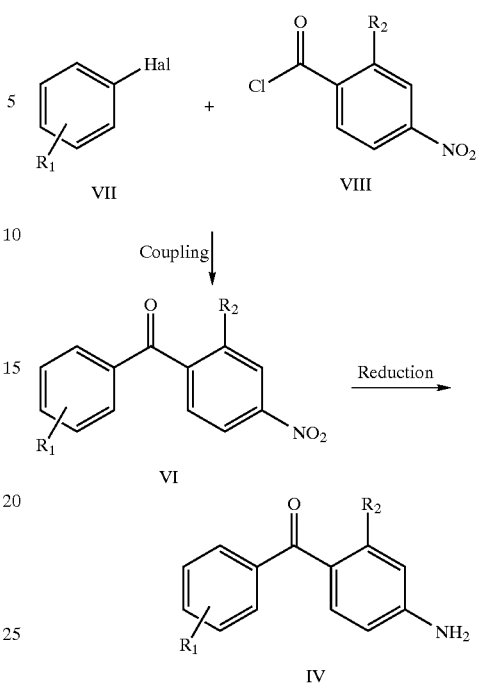

hal: Br, I
and $R_1$ and $R_2$ have the above meanings.

Scheme 2

Compounds accordingly to the present invention with the general formula IV may be prepared by several methods known to those skilled in the art of organic synthesis. One useful sequence is shown in Scheme 2. The key step comprises coupling of a bromide (or iodide) with the general formula VII with an acid chloride with the general formula VIII to afford the benzophenone with the general formula VI. This compound VI may then be reduced to the corresponding amine with the general formula IV by treatment with standard reducing agents. Examples of such reducing agents include, but are not limited to, stannous chloride dihydrate; hydrogen, ammonium formiate, or hydrazine hydrate and a catalytic amount of palladium on carbon. The coupling reaction is done by transforming the bromide (VII) into a reactive organometallic intermediate, e.g. by treatment with butyllithium to afford the lithium derivative or by treatment with magnesium to afford the magnesium derivative. The reactivity of this intermediate is then modulated by transmetallation to e.g. zinc, by treatment with $ZnCl_2$, $ZnBr_2$, or $ZnI_2$. This organozinc compound is then coupled with the acid chloride, with the general formula VIII, under the influence of a palladium(0) complex in catalytic amount. Examples of such catalyst include but are not particularly limited to tetrakis(triphenylphosphine)palladium(0), tetrakis (triphenylarsine)palladium(0), dichlorobis (triphenylphosphine)palladium(II), or benzylchlorobis (triphenylphosphine)palladium(II).

It may be more advantageous in some cases to alter the sequence of the processes described above. The described sequence of processes is not considered as being limited for the preparation of the compounds of the present invention with the general formula I and alteration of the reaction sequence is an obvious alternative for those skilled in the art of organic synthesis.

The present compounds are intended for use in pharmaceutical compositions which are useful in the treatment of the above mentioned diseases and conditions. The amount required of a compound of formula I (hereinafter referred to as the active ingredient) for therapeutic effect will, of course, vary both with the particular compound, the route of administration and the mammal under treatment. A suitable dose of a compound of formula I for systemic treatment is 0.1 to 200 mg/kg bodyweight, the most preferred dosage being 0.2 to 50 mg/kg of mammal bodyweight, administered one or more times daily. A suitable dose of a compound of formula I for topical treatment is 0.1 to 200 mg/kg bodyweight, the most preferred dosage being 0.2 to 50 mg/kg of mammal bodyweight, administered one or more times daily.

While it is possible for an active ingredient to be administered alone as the raw chemical, it is preferable to present it as a pharmaceutical formulation or composition. Conveniently, the active ingredient comprises from 0.1% to 100% by weight of the formulation. Conveniently, dosage units of a formulation contain between 0.07 mg and 1 g of the active ingredient. For topical administration, the active ingredient preferably comprises from 1% to 20% by weight of the formulation but the active ingredient may comprise as much as 50% w/w. Formulations suitable for nasal or buccal administration may comprise 0.1% to 20% w/w. for example about 2% w/w of active ingredient.

By the term "dosage unit" is meant a unitary, i.e. a single dose which is capable of being administered to a patient, and which may be readily handled and packed, remaining as a physically and chemically stable unit dose comprising either the active material as such or a mixture of it with solid or liquid pharmaceutical diluents or carriers.

The formulations, both for veterinary and human medical use, of the present invention comprise an active ingredient in association with a pharmaceutically acceptable carrier therefore and optionally other therapeutic ingredient(s). The carrier(s) must be "acceptable" in the sense of being compatible with the other ingredients of the formulations and not deleterious to the recipient thereof.

The formulations include those in a form suitable for oral, ophthalmic, rectal, parenteral (including subcutaneous, intramuscular and intravenous), transdermal, intra-articular, topical, nasal, or buccal administration.

The formulations may conveniently be presented in dosage unit form and may be prepared by any of the methods well known in the art of pharmacy. All methods include the step of bringing the active ingredient into association with the carrier which constitutes one or more accessory ingredients. In general, the formulations are prepared by uniformly and intimately bringing the active ingredient into association with a liquid carrier or a finely divided solid carrier or both, and then, if necessary, shaping the product into the desired formulation.

Formulations of the present invention suitable for oral administration may be in the form of discrete units as capsules, sachets, tablets or lozenges, each containing a predetermined amount of the active ingredient; in the form of a powder or granules; in the form of a solution or a suspension in an aqueous liquid or non-aqueous liquid; or in the form of an oil-in-water emulsion or a water-in-oil emulsion. The active ingredient may also be administered in the form of a bolus, electuary or paste.

Formulations for rectal administration may be in the form of a suppository incorporating the active ingredient and a carrier such as cocoa butter, or in the form of an enema.

Formulations suitable for parenteral administration conveniently comprise a sterile oily or aqueous preparation of the active ingredient which is preferably isotonic with the blood of the recipient.

Formulations suitable for intra-articular administration may be in the form of a sterile aqueous preparation of the active ingredient which may be in microcrystalline form, for example, in the form of an aqueous microcrystalline suspension. Liposomal formulations or biodegradable polymer systems may also be used to present the active ingredient for both intra-articular and ophthalmic administration.

Formulations suitable for topical administration include liquid or semi-liquid preparations such as liniments, lotions, gels, applicants, oil-in-water or water-in-oil emulsions such as creams, ointments or pastes; or solutions or suspensions such as drops.

Formulations suitable for administration to the nose or buccal cavity include powder, selfpropelling and spray formulations, such as aerosols and atomizers.

In addition to the aforementioned ingredients, the formulations of this invention may include one or more additional ingredients, such as other therapeutically active compounds applied in the treatment of the above mentioned pathological conditions, especially in the treatment of acne, for instance benzoyl peroxide, azelaic acid, topical and systemic antibiotics, such as fusidic acid (Fucidin®), clindamycin, erythromycin, and tetracyclin, retinoids, such as adapalene, tretinoin, isotretinoin, hormones, such as estrogen, and vitamin D.

The novel compounds of the invention are of value in the human and veterinary practice as systemic and topical therapeutic agents for the treatment and prevention of diseases. The novel compounds show anti-acne properties and, i.a., anti-inflammatory and cytokine regulating effects possibly due to MAP kinase inhibition, and are useful in the treatment and prophylaxis of asthma, allergy, arthritis, including rheumatoid arthritis and spondyloarthritis, gout, atherosclerosis, chronic inflammatory bowel disease (Crohn's disease), proliferative and inflammatory skin disorders, such as psoriasis, atopic dermatitis, uveitis, septic shock, AIDS, and osteoporosis.

The invention further relates to the use of an inhibitor of interleukin 1 β (IL-1β) and/or tumour necrosis factor α (TNF-α) secretion, said inhibitor possibly being an inhibitor of intra or extra cellular MAP kinase, in the preparation of a medicament for the treatment and/or prophylaxis of acne and related skin disorders.

The invention will now be further described in the following non-limiting general procedures, preparations and examples.

EXAMPLES

General Procedures, Preparations and Examples

The compounds listed in table 3 are previously disclosed compounds and compound 101 covered by the general formula I, having surprising effect in the acne models described herein. All melting points are uncorrected. For $^1$H and $^{13}$C nuclear magnetic resonance (NMR) spectra (300 MHz) chemical shift values (d) are quoted, unless otherwise specified, for deuteriochloroform ($CDCl_3$) and hexadeuterodimethylsulfoxide (DMSO-$d_6$) solutions relative to internal tetramethylsilane (δ 0.00) or chloroform ($^1$H NMR d 7.25, $^{13}$C NMR δ 76.81). The value for a multiplet (m), either defined (doublet (d), triplet (t), quartet (q)) or not at the approximate mid point is given unless a range is quoted (s singlet, b broad). Chromatography was performed on silica gel.

TABLE 4

Compounds of general formula I

| Comp. No. | Ex. No. | R₁ | R₂ | R₃ | R₆ |
|---|---|---|---|---|---|
| 101,EO1428 | 1 | 2-CH₃ | 2-Cl | 4-Br | H |
| 102,EO1531 | 2 | 2-CH₃ | 2-Cl | 4-F | H |
| 112,EO1388 | 3 | 2-Cl, 4-OCH₃ | 2-Cl | H | H |
| 113,EO1390 | 4 | 2-Cl, 3-Cl, 4-OCH₃ | 2-Cl | H | H |
| 114,EO1394 | 5 | 2-Cl, 6-Cl, 4-OCH₃ | 2-Cl | H | H |
| 115,EO1401 | 6 | 2-OH | 2-Cl | H | H |
| 116,EO1403 | 7 | 2-F | 2-Cl | H | H |
| 117,EO1422 | 8 | 2-Cl, 4-OH | 2-Cl | H | H |
| 118,EO1774 | 9 | 2-CH₃, 4-OCH₂CH₃ | 2-Cl | 4-Br | H |
| 119,EO1776 | 10 | 2-CH₃ | 2-OCH₂CH₃ | 4-Br | H |
| 120,EO1451 | 11 | 2-Cl, 4-Cl, 6-OH | 2-Cl | H | H |
| 121,EO1474 | 12 | 2-CH₃ | 2-Cl | 5-OH | H |
| 122,EO1484 | 13 | 2-OCH₃ | 2-F | H | H |
| 123,EO1486 | 14 | 2-CH₃ | 2-F | H | H |
| 124,EO1508 | 15 | 2-CH₃ | 2-Cl | 5-OCH₃ | H |
| 125,EO1519 | 16 | 2-CH₃ | 2-Cl | 5-Cl | H |
| 126,EO1525 | 17 | 2-CH₃ | 2-Cl | 4-CF₃ | H |
| 127,EO1444 | 18 | 2-CH₃ | 2-Cl | 3-F | H |
| 128,EO1561 | 19 | 2-CH₃ | 2-Cl | H | CH₃ |
| 129,EO1565 | 20 | 2-CH₃ | 2-CH₃ | H | H |
| 130,EO1573 | 21 | 2-CH₃ | 2-Cl | 4-F | CH₃ |
| 131,EO1615 | 22 | 2-CH₃ | 2-Cl | 6-CH₃ | H |
| 132,EO1616 | 23 | 2-CH₃ | 2-Cl | 4-OCH₃ | H |
| 133,EO1671 | 24 | 2-CH₃, 3-F | 2-Cl | H | H |
| 134,JF0002 | 25 | 2-CH₃, 3-CH₃ | 2-Cl | 4-Br | H |
| 135,EO1757 | 26 | 2-CH₃, 4-(CH₂)₃CH₃ | 2-Cl | 4-Br | H |
| 136,EO1758 | 27 | 2-CH₃, 4-Cl | 2-Cl | 4-Br | H |
| 137,EO1766 | 28 | 2-CH₃ | 2-F | 4-Br | H |
| 138,EO1764 | 29 | 2-CH₃, 4-CH₃, 5-CH₃ | 2-Cl | 4-Br | H |
| 139,EO1770 | 30 | 2-CH₃, 4-F | 2-Cl | 4-Br | H |
| 140,EO1769 | 31 | 2-CH₃, 5-CH₃ | 2-Cl | 4-Br | H |
| 141,EO1778 | 32 | 2-CH₃, 3-Cl | 2-Cl | 4-Br | H |
| 142,EO1777 | 33 | 2-CH₃, 4-OCH₃ | 2-F | 4-Br | H |

The numbering in table 4 refers to the numbering in formula I below

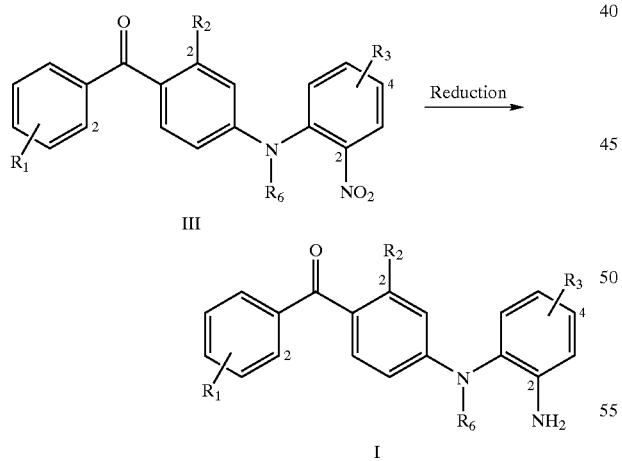

in which $R_1$, $R_2$, $R_{31}$ and $R_6$ have the above meanings.

Scheme 1: Synthesis of Compounds of the General Formula I

General Procedure 1

Reduction of nitro groups in compounds of the general formula III to the corresponding amino compounds of the general formula I by treatment with stannous chloride dihydrate.

A mixture of a nitro compound (5 mmol) and stannous chloride dihydrate (5.64 g, 25 mmol) in absolute ethanol (50 ml) was heated to 70° C. under argon. After 1 hour the starting material has disappeared and the solution was allowed to cool to room temperature and then poured into ice. The pH was made slightly alkaline by the addition of saturated sodium bicarbonate (50 ml) before being extracted with ethyl acetate (3×100 ml). The organic phase was dried (MgSO₄), filtered and evaporated to afford the crude product. The crude product was further purified either by crystallisation or flash 1§ chromatography to yield the title compound.

Example 1

4-(2-Amino-4-bromophenylamino)-2-chloro-2'-methylbenzophenone (Compound 101)

General Procedure: 1

Starting compound III: 4-(4-Bromo-2-nitrophenylamino)-2-chloro-2'-methylbenzophenone Purification: Trituration from a mixture diethylether/pentane 1:1

Mp: 115–116° C. ¹³C NMR (CDCl₃): δ 196.5, 149.0, 144.3, 139.1, 137.9, 135.2, 133.6, 131.3, 130.9, 129.7, 128.8, 128.4, 125.3, 124.3, 121.9, 120.7, 118.9, 115.5, 111.9, 20.4.

Example 2

4-(2-Amino-4-fluorophenylamino)-2-chloro-2'-methylbenzophenone (Compound 102)

General Procedure 1

Starting compound III: 4-(4-Fluoro-2-nitrophenylamino)-2-chloro-2'-methylbenzophenone Purification: Flash chromatography using ethyl acetate/pentane 1:4 as eluent ¹³C NMR (CDCl₃): δ 196.6, 162.3, 149.9, 145.2, 139.3, 137.8, 135.3, 133.7, 131.2, 30.8, 29.6, 129.3, 128.4, 125.3, 120.7, 115.1, 111.5, 105.5, 102.6, 20.4.

Example 3

4-(2-Aminophenylamino)-2,2'-dichloro-4'-methoxybenzophenone (Compound 112)

General Procedure: 1

Starting compound III: 2,2'-Dichloro-4'-methoxy-4-(2-nitrophenylamino)benzophenone Purification: Trituration in diethylether Mp: 149–151° C.; ¹³C NMR (CDCl₃): δ 192.5, 161.9, 149.7, 142.8, 135.3, 133.9, 133.8, 132.1, 131.7, 127.7, 127.6, 126.9, 125.2, 119.1, 116.4, 115.6, 115.2, 112.6, 111.9, 55.7.

Example 4

4'-(2-Aminophenylamino)-2,2',3-trichloro-4-methoxybenzophenone (Compound 113)

General Procedure: 1

Starting compound III: 2,2',3-Trichloro-4-methoxy-4'-(2-nitrophenylamino)benzophenone Purification: Trituration in dichloromethane Mp: 218–219° C.; ¹³C NMR (DMSO-d₆): δ 189.9, 156.9, 151.5, 143.9, 134.5, 133.3, 129.9, 128.4, 126.7, 126.2, 123.7, 123.3, 120.7, 116.3, 115.5, 114.3, 111.3, 110.9, 56.8.

Example 5

4'-(2-Aminophenylamino)-2,2', 6-trichloro-4-methoxybenzophenone (Compound 114)

General Procedure: 1

Starting compound III: 2,2',6-Trichloro-4-methoxy-4'-(2-nitrophenylamino)benzophenone Purification: Trituration in diethylether Mp: 185–186° C.; $^{13}$C NMR (CDCl$_3$): δ 189.1, 160.2, 150.8, 142.9, 136.9, 135.1, 132.6, 132.0, 128.0, 127.2, 124.9, 124.6, 119.2, 116.5, 115.7, 114.1, 112.0, 55.9.

Example 6

4-(2-Aminophenylamino)-2-chloro-2'-hydroxybenzophenone (Compound 115)

General Procedure: 1

Starting compound III: 2–Chloro-2'-hydroxy-4-(2-nitrophenylamino)benzophenone

Purification: Flash chromatography using ethyl acetate/pentane 1:4 as eluent $^{13}$C NMR (CDCl$_3$): δ 200.2, 163.1, 148.8, 142.9, 136.6, 133.7, 133.1, 131.1, 127.6, 127.2, 126.9, 125.5, 119.9, 119.2, 118.8, 118.2, 116.4, 115.0, 112.0.

Example 7

4-(2-Aminophenylamino)-2-chloro-2'-fluorobenzophenone (Compound 116)

General Procedure: 1

Starting compound III: 2–Chloro-2'-fluoro-4-(2-nitrophenylamino)benzophenone

Purification: Flash chromatography using ethyl acetate/pentane 1:4 as eluent $^{13}$C NMR (CDCl$_3$): δ 190.9, 160.5, 149.7, 142.9, 135.0, 133.5, 133.4, 131.0, 128.1, 127.7, 127.0, 125.2, 124.3, 124.2, 119.2, 116.4, 116.2, 115.1, 111.9.

Example 8

4-(2-Aminophenylamino)-2.2'-dichloro-4'-hydroxybenzophenone (Compound 117)

A solution of 4-(2-aminophenylamino)-2,2'-dichloro-4'-methoxybenzophenone (Compound 112) (1.00 g, 2.6 mmol) in dichloromethane (40 ml) was cooled to –78° C. under argon. Borontribromide (1.0 ml, 10.4 mmol) in dichloromethane (5 ml) was added dropwise under stirring. After 15 min the reaction mixture was allowed to come to room temperature over 1 h, and then at 45° C. for 16 hours. The reaction mixture was poured into saturated NaHCO$_3$ and then extracted with EtOAc several times. The organic phases was collected, dried (MgSO$_4$), filtered, and concentrated in vacuo to give the crude product. Concentration in vacuo from a solution of methanol removed traces of boric acid. The crude product was further purified by flash chromatography using EtOAc/pentane 3:2 as eluent.

$^{13}$C NMR (DMSO-d$_6$): δ 191.1, 160.3, 151.0, 144.0, 133.9, 133.8, 132.2, 132.1, 129.9, 126.6, 126.2, 125.0, 124.2, 116.7, 116.5, 115.6, 114.3, 114.2, 111.4.

Example 9

4-(2-Amino-4-bromophenylamino)-2-chloro-4'-ethoxy-2'-methylbenzophenone (Compound 118)

General Procedure: 1

Starting compound III: 4-(4-Bromo-2-nitrophenylamino)-2-chloro-4'-ethoxy-2'-methylbenzophenone Purification: A solution of the crude product was filtered through a pad of silica gel and then concentrated in vacuo $^{13}$C NMR (CDCl$_3$): δ 195.5, 161.3, 148.3, 144.2, 141.9, 134.3, 133.6, 132.5, 130.8, 130.2, 128.2, 124.7, 121.9, 120.5, 118.9, 117.6, 115.2, 112.1, 110.8, 63.5, 21.5, 14.7.

Example 10

4-(2-Amino-4-bromophenylamino)-2-ethoxy-2'-methylbenzophenone (Compound 119)

General Procedure: 1

Starting compound III: 4-(4-Bromo-2-nitrophenylamino)-2-ethoxy-2'-methylbenzophenone Purification: A solution of the crude product was filtered through a pad of silica gel and then concentrated in vacuo $^{13}$C NMR (CDCl$_3$): δ 196.9, 161.0, 150.8, 144.2, 142.7, 135.6, 133.6, 130.3, 129.1, 128.1, 127.4, 124.9, 121.8, 120.2, 120.0, 118.8, 106.6, 97.5, 63.7, 19.8, 13.8.

Example 11

4'-(2-Aminophenylamino)-2.2', 4-trichloro-6-hydroxybenzophenone (Compound 120)

General Procedure: 1

Starting compound III: 2,2',4-Trichloro-6-hydroxy-4-(2-nitrophenylamino)benzophenone Purification: Trituration in dichloromethane Mp: 141–143° C.; $^{13}$C NMR (CDCl$_3$+1 drop CD$_3$OD): δ 193.1, 158.1, 150.9, 142.7, 137.2, 135.9, 134.3, 133.5, 127.7, 127.0, 126.2, 125.3, 124.6, 121.2, 119.3, 116.7, 115.8, 115.4, 111.9.

Example 12

4-(2-Amino-5-hydroxyphenylamino)-2-chloro-2'-methylbenzophenone (Compound 121)

General Procedure: 1

Starting compound III: 2–Chloro-4-(5-(methoxymethyloxy)-2-nitrophenylamino)-2'-methylbenzophenone Purification: Flash chromatography using ethyl acetate/pentane 1:1 as eluent $^{13}$C NMR (CDCl$_3$+1 drop CD$_3$OD): δ 197.2, 150.3, 149.5, 139.4, 137.7, 135.3, 134.1, 133.9, 131.3, 130.9, 129.6, 127.8, 127.5, 125.4, 118.4, 115.6, 114.0, 112.4, 112.0, 20.3.

Example 13

4-(2-Aminophenylamino)-2-fluoro-2'-methoxybenzophenone (Compound 122)

General Procedure: 1

Starting compound III: 2-Fluoro-2'-methoxy-4-(2-nitrophenylamino)benzophenone

Purification: Flash chromatography using ethyl acetate/pentane 1:2 as eluent $^{13}$C NMR (CDCl$_3$): δ 191.3, 164.0, 157.4, 151.8, 142.8, 133.5, 131.7, 131.2, 129.2, 127.7, 127.0, 125.3, 120.5, 119.2, 117.8, 116.5, 111.3, 109.6, 100.3, 55.7.

Example 14

4-(2-Aminophenylamino)-2-fluoro-2'-methylbenzophenone (Compound 123)

General Procedure: 1

Starting compound III: 2-Fluoro-2'-methyl-4-(2-nitrophenylamino)benzophenone

Purification: Trituration in a mixture of diethylether/pentane (1:1)

Mp: 150–152° C.; $^{13}$C NMR (CDCl$_3$): δ 194.3, 163.9, 152.2, 142.9, 140.7, 136.2, 133.9, 130.8, 130.0, 128.0, 127.9, 127.2, 125.3, 125.0, 119.2, 1172, 116.5, 109.7, 100.6, 19.8.

Example 15

4-(2-Amino-5-methoxyphenylamino)-2-chloro-2'-methylbenzophenone (Compound 124)

General Procedure: 1

Starting compound III: 2–Chloro-4-(5-methoxy-2-nitrophenylamino)-2'-5 methylbenzophenone Purification: Flash chromatography using ethyl acetate/pentane 1:2 as eluent $^{13}$C NMR (CDCl$_3$): δ 196.5, 153.3, 148.9, 139.3, 137.8, 135.5, 135.2, 133.7, 131.2, 130.8, 129.6, 128.5, 126.9, 125.3, 117.8, 115.7, 112.8, 112.1, 111.2, 55.8, 20.4.

Example 16

4-(2-Amino-5-chlorophenylamino)-2-chloro-2'-methylbenzophenone (Compound 125)

General Procedure: 1

Starting compound III: 2–Chloro-4-(5-chloro-2-nitrophenylamino)-2'-methylbenzophenone Purification: Flash chromatography using ethyl acetate/pentane 1:3 and then 1:2 as eluent $^{13}$C NMR (CDCl$_3$): δ 196.6, 148.6, 141.2, 139.1, 137.9, 135.1, 133.6, 131.3, 130.9, 129.7, 129.0, 127.3, 126.5, 126.2, 125.4, 123.2, 117.2, 115.8, 112.1, 20.4.

Example 17

4-(2-Amino-4-(trifluoromethyl)phenylamino)-2-chloro-2'-methylbenzophenone (Compound 126)

General Procedure: 1

Starting compound III: 2–Chloro-4-(4-(trifluoromethyl)-2-nitrophenylamino)-2'-methylbenzophenone Purification: Flash chromatography using ethyl acetate/pentane 1:5 as eluent $^{13}$C NMR (CDCl$_3$): δ 196.6, 148.0, 142.0, 138.9, 138.0, 135.0, 133.4, 131.4, 131.0, 129.8, 129.5, 129.0, 125.4, 125.2, 124.0, 116.3, 115.9, 115.9, 113.1, 112.7, 20.5.

Example 18

4-(2-Amino-3-fluorophenylamino)-2-chloro-2'-methylbenzophenone (Compound 127)

General Procedure: 1

Starting compound III: 2–Chloro-4-(3-fluoro-2-nitrophenylamino)-2'-methylbenzophenone Purification: Flash chromatography using ethyl acetate/pentane 1:6 as eluent $^{13}$C NMR (CDCl$_3$): δ 196.6, 152.3, 148.8, 139.2, 137.9, 135.1, 133.6, 131.4, 131.3, 130.8, 129.7, 128.8, 127.4, 125.4, 121.5, 117.8, 115.7, 113.1, 112.1, 20.4.

Example 19

4-(2-Amino-N-methyl-phenylamino)-2-chloro-2'-methylbenzophenone (Compound 128)

General Procedure: 1

Starting compound III: 2–Chloro-2'-methyl-4-(N-methyl-2-nitrophenylamino)benzophenone Purification: Flash chromatography using ethyl acetate/pentane 1:4 as eluent $^{13}$C NMR (CDCl$_3$): δ 196.5, 151.8, 143.3, 139.7, 137.5, 135.3, 133.7, 131.7, 131.1, 130.5, 129.3, 128.6, 128.2, 126.6, 125.3, 119.6, 116.5, 114.2, 110.6, 38.7, 20.3.

Example 20

4-(2-Aminophenylamino)-2.2'-dimethylbenzophenone (Compound 129)

General Procedure: 1

Starting compound III: 2,2'-Dimethyl-4-(2-nitrophenylamino)benzophenone

Purification: Flash chromatography using ethyl acetate/pentane 1:4 as eluent $^{13}$C NMR (CDCl$_3$): δ 199.1, 148.9, 142.9, 142.7, 141.1, 136.4, 135.3, 130.8, 129.6, 128.4, 128.2, 127.2, 126.7, 126.0, 125.2, 119.1, 116.9, 116.3, 110.3, 22.2, 19.9.

Example 21

4-(2-Amino-4-fluoro-N-methyl-phenylamino)-2-chloro-2'-1methylbenzophenone (Compound 130)

General Procedure: 1

Starting compound III: 2–Chloro-4-(4-fluoro-N-methyl-2-nitro-phenylamino)-2'-methylbenzophenone Purification: Flash chromatography using ethyl acetate/pentane 1:6 as eluent $^{13}$C NMR (CDCl$_3$): δ 196.5, 162.5, 151.9, 145.0, 139.5, 137.6, 135.3, 133.7, 131.2, 130.6, 129.6, 129.4, 127.7, 126.9, 125.3, 114.3, 110.6, 106.0, 102.8, 38.9, 20.3.

Example 22

4-(2-Amino-6-methylphenylamino)-2-chloro-2'-methylbenzophenone (Compound 131)

General Procedure: 1

Starting compound III: 2–Chloro-2'-methyl-4-(6-methyl-2-nitrophenylamino)benzophenone Purification: Flash chromatography using ethyl acetate/pentane 1:2 as eluent Mp: 136–137° C.; $^{13}$C NMR (CDCl$_3$): δ 196.5, 149.9, 144.5, 139.4, 137.7, 137.5, 135.5, 134.0, 131.2, 130.6, 129.5, 128.2, 127.9, 125.3, 123.1, 120.5, 114.4, 113.7, 110.8, 20.3, 18.1.

Example 23

4-(2-Amino-4-methoxyphenylamino)-2-chloro-2'-methylbenzophenone (Compound 132)

General Procedure: 1

Starting compound III: 2–Chloro-4-(4-methoxy-2-nitrophenylamino)-2'-methylbenzophenone Purification: Flash chromatography using ethyl acetate/dichloromethane 1:100 as eluent $^{13}$C NMR (CDCl$_3$): δ 196.5, 159.6, 150.6, 144.8, 139.5, 137.7, 135.4, 133.8, 131.2, 130.6, 129.5, 129.3, 127.8, 125.3, 118.0, 114.8, 111.3, 104.5, 101.3, 55.4, 20.4.

Example 24

4-(2-Aminophenylamino)-2-chloro-3'-fluoro-2'-methylbenzophenone (Compound 133)

General Procedure: 1

Starting compound III: 2–Chloro-3'-fluoro-2'-methyl-4-(2-nitrophenylamino)benzophenone Purification: Flash chromatography using ethyl acetate/pentane 1:4 as eluent and then Trituration in a mixture of ethylacetate/pentane 1:10

Mp: 94–96° C.;

$^{13}$C NMR (CDCl$_3$): δ 195.1, 161.6, 150.0, 142.9, 142.1, 135.6, 134.1, 127.8, 127.5, 127.0, 126.5, 125.1, 124.6, 124.5, 119.2, 117.2, 116.5, 115.4, 111.8, 11.5.

Example 25

4-(2-Amino-4-bromophenylamino)-2-chloro-2',3'-dimethylbenzophenone (Compound 134)

General Procedure: 1

Starting compound III: 4-(4-Bromo-2-nitrophenylamino)-2-chloro-2',3'-dimethylbenzophenone Purification: Flash chromatography using dichloromethane as eluent $^{13}$C NMR (CDCl$_3$): δ 197.1, 149.3, 144.3, 140.4, 137.9, 135.5, 135.5, 134.2, 132.0, 128.4, 128.3, 126.5, 125.0, 124.2, 121.8, 120.7, 118.8, 115.6, 111.8, 20.2, 16.5.

Example 26

4-(2-Amino-4-bromophenylamino)-4'-n-butyl-2-chloro-2'-methylbenzophenone (Compound 135)

General Procedure: 1

Starting compound III: 4-(4-Bromo-2-nitrophenylamino)-4'-n-butyl-2-chloro-2'-methylbenzophenone Purification: Flash chromatography using ethylacetate/pentane 1:3 as eluent $^{13}$C NMR (CDCl$_3$): δ 196.4, 148.6, 146.5, 144.3, 138.5, 136.1, 134.8, 133.1, 131.6, 130.6, 129.4, 128.2, 125.3, 124.5, 121.9, 120.5, 118.8, 115.4, 111.9, 35.6, 33.3, 22.4, 20.7, 13.9.

Example 27

4-(2-Amino-4-bromophenylamino)-2.4'-dichloro-2'-methylbenzophenone (Compound 136)

General Procedure: 1

Starting compound III: 4-(4-Bromo-2-nitrophenylamino)-2, 4'-dichloro-2'-methylbenzophenone Purification: Flash chromatography using ethyl acetate/pentane 1:4 as eluent and then Trituration in a mixture of diethylether/pentane Mp: 136–137° C.;

$^{13}$C NMR (CDCl$_3$): δ 195.4, 149.2, 144.3, 140.0, 137.6, 136.7, 135.2, 133.5, 131.3, 131.0, 128.4, 125.6, 124.2, 122.0, 120.8, 118.9, 115.4, 112.0, 20.3.

Example 28

4-(2-Amino-4-bromophenylamino)-2-fluoro-2'-methylbenzophenone (Compound 137)

General Procedure: 1

Starting compound III: 4-(4-Bromo-2-nitrophenylamino)-2-fluoro-2'-methylbenzophenone Purification: Filtered through a pad of silica gel using ethylacetate as solvent $^{13}$C NMR (CDCl$_3$): δ 194.3, 163.8, 151.6, 144.3, 140.4, 136.3, 133.9, 130.9, 130.1, 128.6, 128.1, 125.3, 124.0, 121.9, 121.0, 118.9, 117.7, 109.8, 100.8, 19.9.

Example 29

4'-(2-Amino-4-bromophenylamino)-2'-chloro-2.4, 5-trimethylbenzophenone (Compound 138)

General Procedure: 1

Starting compound III: 4'-(4-Bromo-2-nitrophenylamino)-2'-chloro-2, 4, 5-trimethylbenzophenone Purification: Flash chromatography using ethyl acetate/pentane 1:3 as eluent $^{13}$C NMR (CDCl$_3$): δ 196.5, 148.5, 144.2, 140.2, 136.3, 135.8, 134.8, 133.4, 133.1, 132.8, 131.5, 129.6, 128.2, 124.6, 122.0, 120.6, 118.9, 115.4, 112.0, 20.1, 19.7, 19.1.

Example 30

4-(2-Amino-4-bromophenylamino)-2-chloro-4'-fluoro-2'-methylbenzophenone (Compound 139)

General Procedure: 1

Starting compound III: 4-(4-Bromo-2-nitrophenylamino)-2-chloro-4'-fluoro-2'-methylbenzophenone Purification: Filtered through a pad of silica gel using ethylacetate as solvent $^{13}$C NMR (CDCl$_3$): δ 195.3, 164.0, 149.0, 144.3, 141.7, 135.2, 135.0, 133.2, 132.4, 128.9, 128.4, 124.3, 122.0, 120.8, 118.9, 118.2, 115.4, 112.3, 112.0, 20.7.

Example 31

4-(2-Amino-4-bromophenylamino)-2-chloro-2',5'-dimethylbenzophenone (Compound 140)

General Procedure: 1

Starting compound III: 4-(4-Bromo-2-nitrophenylamino)-2-chloro-2', 5'-dimethylbenzophenone Purification: Filtered through a pad of silica gel using ethylacetate as solvent $^{13}$C NMR (CDCl$_3$): δ 196.7, 148.9, 144.2, 139.1, 135.1, 134.9, 134.7, 133.6, 131.6, 131.2, 130.0, 128.9, 128.3, 124.4, 122.0, 120.7, 118.9, 115.5, 111.9, 20.8, 19.9.

Example 32

4-(2-Amino-4-bromophenylamino)-2.3'-dichloro-2'-methylbenzophenone (Compound 141)

General Procedure: 1

Starting compound III: 4-(4-Bromo-2-nitrophenylamino)-2,3'-dichloro-2'-methylbenzophenone Purification: Filtered through a pad of silica gel using ethylacetate as solvent $^{13}$C NMR (CDCl$_3$): δ 195.3, 149.6, 144.3, 142.1, 135.9, 135.9, 134.9, 134.3, 131.1, 128.5, 127.6, 126.8, 126.4, 123.9, 122.0, 121.0, 118.9, 115.6, 111.9, 17.1.

Example 33

4-(2-Amino-4-bromophenylamino)-2-fluoro-4'-methoxy-2'-methylbenzophenone (Compound 142)

General Procedure: 1

Starting compound III: 4-(4-Bromo-2-nitrophenylamino)-2-fluoro-4'-methoxy-2'-methylbenzophenone Purification: Filtered through a pad of silica gel using ethylacetate as solvent $^{13}$C NMR (CDCl$_3$): δ 161.4, 144.3, 140.4, 133.6, 131.9, 128.5, 124.3, 122.0, 120.8, 118.9, 116.6, 110.3, 109.8, 55.3, 20.9.

Example 34

Cream Formulation Containing Compound 101

4-(2-Amino-4-bromophenylamino)-2-chloro-2'-methylbenzophenone (Compound 101, 10 g) was dissolved in diethylenglycolmonoethylether (350 g) and distilled water (350 g) was added. Methylparaben (1 g) and propylparaben (0.2 g) were dissolved in phenoxyethanol (6 g). This solution was mixed with the former solution of Compound 101. Paraffin oil (183 g), cetostearylic alcohol (50 g) and ARLACEL® (50 g) was melted in a vessel at 70 to 80° C. The mixed solutions were likewise heated to 60–70° C. and slowly added to the melted oil phase under high speed stirring. The homogenised components were cooled to room temperature.

Example 35

Tablet Containing Compound 101

| Compound 101 (active substance) | 50 mg |
| --- | --- |
| Lactose | 125 mg |
| Starch | 12 mg |
| Methyl cellulose | 2 mg |
| Sodium carboxymethyl cellulose | 10 mg |
| Magnesium stearate | 1 mg |

The active substance, lactose and starch are mixed to a homogeneous state in a suitable mixer and moistened with a 5 per cent aqueous solution of methyl cellulose 15 cps. The mixing is continued until granules are formed. If necessary, the wet granulation is passed through a suitable screen and dried to a water content of less than 1% in a suitable drier, e.g. fluid bed or drying oven. The dried granules are passed through a 1 mm screen and mixed to a homogeneous state with sodium carboxymethyl cellulose. Magnesium stearate is added, and the mixing is continued for a short period of time. Tablets with a weight of 200 mg are produced from the granulation by means of a suitable tabletting machine.

Example 36

Formulation for Injection Containing Compound 101

| Compound 101 (active substance) | 1% |
| --- | --- |
| Sodium chloride | q.s. |
| Ethanol | 10% |
| Water for injection to make | 100% |

The active substance is dissolved in ethanol (10%) then water for injection made isotonic with sodium chloride is added to make 100%. The mixture is filled into ampoules and sterilised.

Example 37

Cream Formulation Containing Compound 101

Compound 101 (10 g) was dissolved in Octyldodecyl myristate (250 g) to form Part A. Methylparaben (1 g) and propylparaben (0.2 g) were dissolved in phenoxyethanol (6 g) and mixed with a 0.025 M Phosphate buffer pH=7.5 (632, 8 g) to form Part B. Cetostearyl alcohol (50 g) and ARLACEL 165® (50 g) was melted in a vessel at 70 to 80° C. Part A was added and heated to 60–70° C. The aqueous phase were likewise heated to 60–70° C. and slowly added to the melted oil phase under high speed stirring. The homogenised components were cooled to room temperature.

Example 38

Cream Formulation Containing Compound 101— Pemulen Based

Compound 101 (10 g) was dissolved in Octyldodecyl myristate (250 g) and sorbitan oleate (3 g) was added to form Part A. Pemulen TR-2 (3 g) and Carbopol 980 (3 g) were dispersed in Part A in order to break-up any soft agglomerates. Methylparaben (1 g) and propylparaben (0.2 g) were dissolved in phenoxyethanol (6 g) and mixed with water (700 g) to form Part B. With moderate agitation Part B was added to Part A and mix 30–40 minutes or until a smooth dispersion is apparent. Add as much Sodium hydroxide in order to obtain a pH of 7.5 and mix vigorously until a smooth product is obtained. Add water to a final volume of 1000 g.

Example 39

Gel Suspension Containing Compound 101

Carbopol 980 (10 g) is dispersed in water (400 g) and neutralised with a sodium hydroxide (10%) to pH=7.5 (Part A). In order to prepare Part B, Methylparaben (1 g) and propylparaben (0.2 g) were dissolved in phenoxyethanol (6 g). Methylcellulose (10 g) is dispersed in cold water (100 g) and hot water is added (300 g), which is termed Part C. Part B and Part C is thoroughly mixed and micronized. Compound 101 (10 g) is dispersed in the combined mixture (Part D). Part D is added to the neutralised gel under mild agitation. Water is added to make a final weight of 1000 gram, the water is thoroughly mixed into the thickened gel using mild agitation.

Example 40

Gel Formulation Containing Compound 101

Carbopol 980 (10 g) and Aerosil R 972 2% is dispersed in water (600 g) and neutralised with a 10% sodium hydroxide solution to pH=7.5 (Part A). In order to prepare Part B, Methylparaben (1 g) and propylparaben (0.2 g) were dissolved in phenoxyethanol (6 g). Compound 101 (10 g) is dissolved in Labrasol (300 g) (Part C). Part B and Part C is combined to form Part D, which is then added to the neutralised gel under mild agitation. Water is added to make a final weight of 1000 gram, the water is thoroughly mixed into the thickened gel using mild agitation.

Example 41

Ointment Formulation Containing Compound 101

Compound 101 (5 g) is dissolved in Octyldodecyl myristate (500 g) to form Part A. Aerosil R 972 (70 g) is then dispersed into Part A by low speed agitation to form part B. Part B is then combined with Vaseline (380 g).

Example 42

Lotion with Ethanol Containing Compound 101

Compound 101 (5 g) is dissolved in Ethanol (500 g) to form Part A. Polyethylene glycol 300 is then dispersed into Part A by low speed agitation.

Example 43

Lotion with Ethanol Containing Compound 101

Compound 101 (15 g) is dissolved in Ethanol (600 g) and Octyldodecyl myristate (100 g) and Water (300 g) is then added to form Part A. Hydroxypropylmethylcellulose is dispersed into Part A by low speed agitation.

What is claimed is:

1. A compound having the general formula I

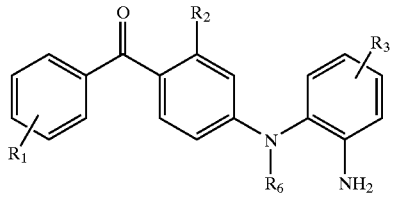

wherein $R_1$ represents one or more, similar or different substituents; selected from the group consisting of hydroxy, F, Cl, Br, and I, $(C_1-C_5)$alkyl, $(C_1-C_5)$alkoxy, $(C_1-C_5)$alkylthio, and cyano, provided that, when $R_1$ represents one substituent, it is in the ortho position, and when $R_1$ represents more than one substituent, at least one, substituent $R_1$ is in the ortho position; $R_2$ represents hydroxy, F, Cl, Br, and I, $(C_1-C_5)$alkyl, $(C_1-C_5)$alkoxy, $(C_1-C_5)$alkylthio, or cyano; $R_3$ represents halogen; and $R_6$ represents hydrogen or methyl; and salts thereof with pharmaceutically acceptable acids, hydrates thereof or solvates.

2. A compound according to claim 1 wherein $R_1$ represents methyl, $R_2$ represents Cl, $R_3$ represents F or Br, and $R_6$ represents hydrogen.

3. A compound according to claim 1, which is selected from the group consisting of:
- 4-(2-Amino-4-bromophenylamino)-2-chloro-2'-methylbenzophenone,
- 4-(2-Amino-4-fluorophenylamino)-2-chloro-2'-methylbenzophenone,
- 4-(2-Amino-4-bromophenylamino)-2-chloro-4'-ethoxy-2'-methylbenzophenone,
- 4-(2-Amino-4-bromophenylamino)-2-ethoxy-2'-methylbenzophenone,
- 4-(2-Amino-5-chlorophenylamino)-2-chloro-2'-methylbenzophenone,
- 4-(2-Amino-3-fluorophenylamino)-2-chloro-2'-methylbenzophenone,
- 4-(2-Amino-4-fluoro-N-methyl-phenylamino)-2-chloro-2'-methylbenzophenone,
- 4-(2-Amino-4-bromophenylamino)-2-chloro-2',3'-dimethylbenzophenone,
- 4-(2-Amino-4-bromophenylamino)-4'-n-butyl-2-chloro-2'-methylbenzophenone,
- 4-(2-Amino-4-bromophenylamino)-2,4'-dichloro-2'-methylbenzophenone,
- 4-(2-Amino-4-bromophenylamino)-2-fluoro-2'-methylbenzophenone,
- 4'-(2-Amino-4-bromophenylamino)-2'-chloro-2,4,5-trimethylbenzophenone,
- 4-(2-Amino-4-bromophenylamino)-2-chloro-4'-fluoro-2'-methylbenzophenone,
- 4-(2-Amino-4-bromophenylamino)-2-chloro-2',5'-dimethylbenzophenone,
- 4-(2-Amino-4-bromophenylamino)-2,3'-dichloro-2'-methylbenzophenone,
- 4-(2-Amino-4-bromophenylamino)-2-fluoro-4'-methoxy-2'-methylbenzophenone, and their salts with pharmaceutically acceptable acids, their hydrates, or solvates.

4. A pharmaceutical preparation, containing a compound according to claim 1 together with the necessary pharmaceutically acceptable carriers and optionally together with a second active ingredient selected from the group consisting of glucocorticoids, vitamin D's, anti-histamines, platelet activating factor (PAF) antagonists, anticolinergic agents, methyl xanthines, β-adrenergic agents, salicylates, indomethacin, flufenamate, naproxen, timegadine, gold salts penicillamine, serum cholesterol-reducing agents, retinoids, zinc salts, and salicylazosulfapyridin (Salazopyrin).

5. A method for the treatment and/or prophylaxis of acne and acne related skin disorders comprising administering to a patient in need thereof a pharmaceutically acceptable amount of a compound of the formula II

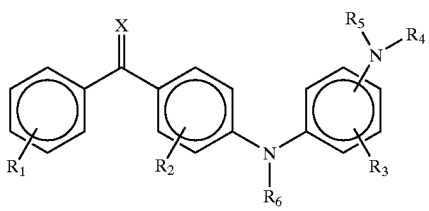

in which formula $R_1$ and $R_2$ independently represent one or more, similar or different substituents selected from the group consisting of hydrogen, halogen, hydroxy, mercapto, trifluoromethyl, amino, $(C_1-C_5)$alkyl, $(C_1-C_5)$alkoxy, $(C_1-C_5)$alkylthio, $(C_1-C_5)$alkylamino, and $(C_1-C_5)$alkoxycarbonyl, cyano, carbamoyl, phenyl, or nitro; and where $R_2$ further can be carboxy; $R_3$ represents hydrogen, halogen, hydroxy, mercapto, trifluoromethyl, amino, $(C_1-C_5)$alkyl, $(C_1-C_5)$alkoxy, $(C_1-C_5)$alkylthio, $(C_1-C_5)$alkylamino, or $(C_1-C_5)$alkoxycarbonyl, phenyl, cyano, carboxy, or carbamoyl; $R_4$, $R_5$ and $R_6$ represent independently hydrogen, trifluoromethyl, $(C_1-C_5)$alkyl, carbamoyl, $(C_1-C_5)$alkoxycarbonyl, or alkaloyl, the C-content of which can be from 1 to 5; X represents oxygen, N—OH, and N—O-alkyl, dialkoxy, cyclic dialkoxy, dialkylthio, or cyclic dialkylthio, in which groups the C-content can be from 1 to 5, and salts thereof with pharmaceutically acceptable, non-toxic acids for the preparation of a medicament for the prophylaxis and/or treatment of acne and acne related skin disorders.

6. A method for the treatment and/or prophylaxis of acne and acne related skin disorders comprising administering. to a patient in need!thereof a phamaceutically acceptable amount of a compound according to claim 5 and selected from the group, consisting of
- 4-(2-Aminophenylamino)-benzophenone,
- 4-(2-aminophenylamino)-2-chloro-2'-methylbenzophenone;
- 4-(2-aminophenylamino)-2-methoxy-2'-methylbenzophenone;
- 4-(2-aminophenylamino)-2-chloro-2'-(trifluoromethyl)benzophenone;
- ethyl N-(2-(4-(2-methylbenzoyl)-3-chlorophenylamino)phenyl)carbamate;

4-(2-aminophenylamino)-2'-chloro-4-methoxy-2,6-dimethylbenzophenone; 2,2,2-trifluoro-N-(2-(4-(2-methylbenzoyl)-3-chlorophenylamino)phenyl)acetamide;

4-(2-aminophenylamino)-2-chloro-2',6'-dimethylbenzophenone;

4-(2-aminophenylamino)-2-chloro-4'-fluoro-2'-methylbenzophenone;

4-(2-Aminophenylamino)-2,2'-dichloro-4'-methoxybenzophenone,

4'-(2-Aminophenylamino)-2,2',3-trichloro-4-methoxybenzophenone,

4'-(2-Aminophenylamino)-2,2',6-trichloro-4-methoxybenzophenone, 4-(2-Aminophenylamino)-2-chloro-2'-hydroxybenzophenone, 4-(2-Aminophenylamino)-2-chloro-2'-fluorobenzophenone, 4-(2-Aminophenylamino)-2,2'-dichloro-4'-hydroxybenzophenone, 4'-(2-Aminophenylamino)-2,2',4-trichloro-6-hydroxybenzophenone, 4-(2-Amino-5-hydroxyphenylamino)-2-chloro-2'-methylbenzophenone, 4-(2-Aminophenylamino)-2-fluoro-2'-methoxybenzophenone, 4-(2-Aminophenylamino)-2-fluoro-2'-methylbenzophenone, 4-(2-Amino-5-methoxyphenylamino)-2-chloro-2'-methylbenzophenone, 4-(2-Amino-4-(trifluoromethyl)phenylamino)-2-chloro-2'-methylbenzophenone, 4-(2-Amino-N-methyl-phenylamino)-2-chloro-2'-methylbenzophenone, 4-(2-Aminophenylamino)-2,2'-dimethylbenzophenone, 4-(2-Amino-6-methylphenylamino)-2-chloro-2'-methylbenzophenone, 4-(2-Amino-4-methoxyphenylamino)-2-chloro-2'-methylbenzophenone, 4-(2-Aminohenylamino)-2-chloro-3'-fluoro-2'-methylbenzophenone, and their salts, for the preparation of a medicament for the prophylaxis and/or treatment of acne and acne related skin disorders.

7. A method for the treatment and/or prophylaxis of acne and acne related skin disorders, characterised in administering to patients suffering from said diseases an effective amount of one or more compounds described in any one of claims 1–6, optionally together or concomitantly with one or more other therapeutically active components selected from the group consisting of benzoyl peroxide, azelaic acid, topical and systemic antibiotics, retinoids, hormones, and vitamin D, and a pharmaceutically acceptable carrier.

8. The method of claim 5, wherein X represents oxygen, N—OH, or N—O-alkyl wherein the C-content is from 1 to 5.

9. The pharmaceutical preparation according to claim 4, wherein the pharmaceutical preparation contains a second active ingredient selected from the group consisting of glucocorticoids, vitamin D's, anti-histamines, platelet activating factor (PAF) antagonists, anticolinergic agents, methyl xanthines, β-adrenergic agents, salicylates, indomethacin, flufenamate, naproxen, timegadine, gold salts penicillamine, serum cholesterol-reducing agents, retinoids, zinc salts, and salicylazosulfapyridin.

* * * * *